(12) United States Patent
Koby et al.

(10) Patent No.: US 7,594,897 B2
(45) Date of Patent: Sep. 29, 2009

(54) KNEE SUPPORT DEVICE

(76) Inventors: Aurelia Koby, 4461 Ocean Blvd., San Diego, CA (US) 92109; Ian MacMorran, 866 Cordova St., San Diego, CA (US) 92107

( * ) Notice: Subject to any disclaimer, the term of this patent is extended or adjusted under 35 U.S.C. 154(b) by 13 days.

(21) Appl. No.: 11/697,586

(22) Filed: Apr. 6, 2007

(65) Prior Publication Data

US 2008/0249450 A1    Oct. 9, 2008

(51) Int. Cl.
| A61F 5/00 | (2006.01) |
| A61F 13/06 | (2006.01) |
| A61F 5/37 | (2006.01) |
| A41D 13/00 | (2006.01) |

(52) U.S. Cl. .............. 602/26; 602/22; 602/23; 602/24; 602/62; 2/22; 2/24; 128/882; 128/892

(58) Field of Classification Search ........... 602/26, 602/16, 23, 62, 19; 24/302; 2/62, 22, 24, 2/908, 911
See application file for complete search history.

(56) References Cited

U.S. PATENT DOCUMENTS

| 3,926,186 A | * | 12/1975 | Nirschl | 602/62 |
| 4,334,528 A | | 6/1982 | Gauvry | |
| D265,590 S | | 7/1982 | Gauvry | |
| 4,425,912 A | * | 1/1984 | Harper | 602/26 |
| 5,024,216 A | * | 6/1991 | Shiono | 602/26 |
| 5,080,095 A | * | 1/1992 | Tungate | 604/113 |
| 5,656,023 A | * | 8/1997 | Caprio et al. | 602/63 |
| 5,800,491 A | * | 9/1998 | Kolen et al. | 607/108 |
| 6,063,048 A | * | 5/2000 | Bodenschatz et al. | 602/62 |
| 6,357,054 B1 | * | 3/2002 | Bainbridge et al. | 2/455 |
| D560,043 S | * | 1/2008 | Nishi | D29/121.1 |
| 2005/0240134 A1 | * | 10/2005 | Brown | 602/26 |

* cited by examiner

*Primary Examiner*—Patricia Bianco
*Assistant Examiner*—Ophelia Hawthorne
(74) *Attorney, Agent, or Firm*—Loza & Loza, LLP; Heidi Eisenhut

(57) ABSTRACT

Broadly, the present invention is a knee support device for providing focused and comfortable pressure (i.e. conforms to the size and shape of the knee and patella) to reduce knee pain. The knee support device comprises a stretchable band for encircling a portion of the user's leg. A moldable inner support is secured to the inner surface of the band and is filled with beads allowing the moldable inner support to conform to the specific anatomy of the user's knee for maximum support and relief. The moldable inner support is only affixed to the band at its ends so that it may move freely with respect to the band and also provides focused pressure to reduce knee pain and helps stabilize the patella to improve alignment and tracking.

12 Claims, 2 Drawing Sheets

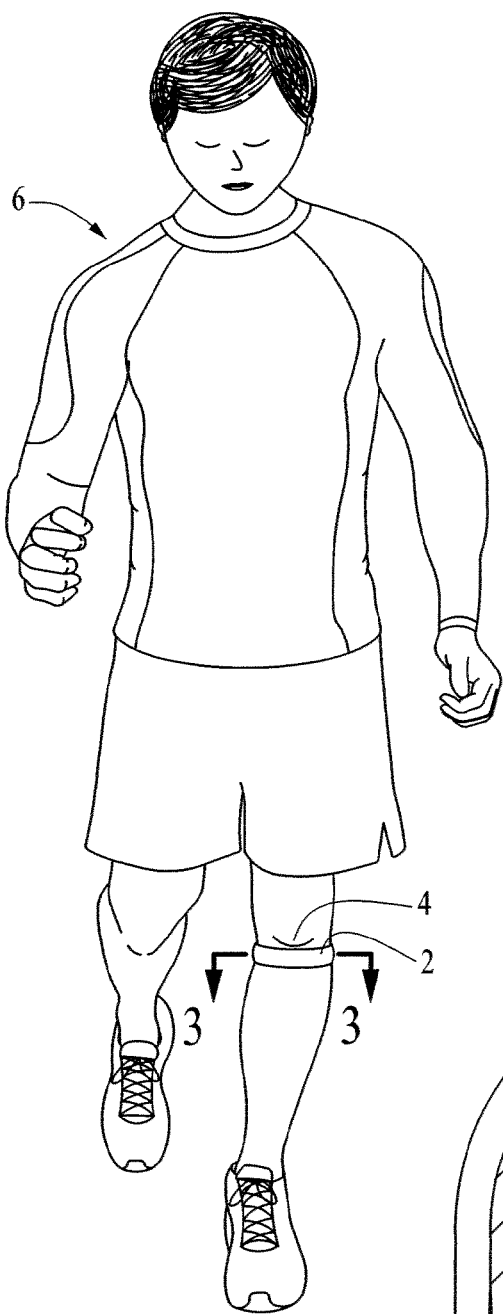
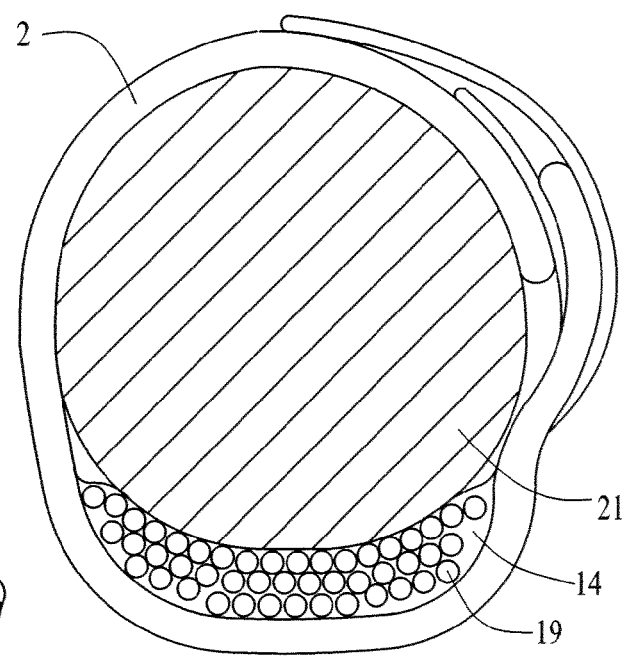
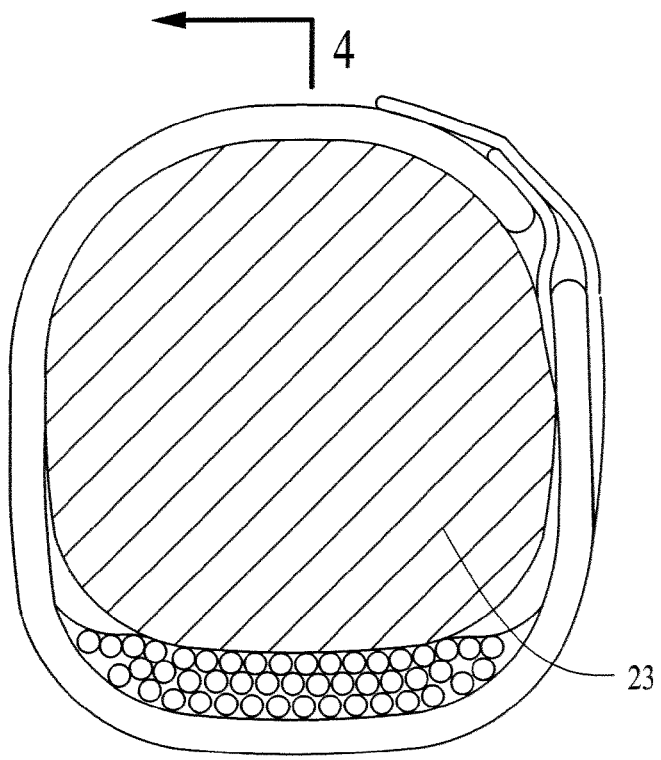
fig. 1
fig. 3A
fig. 3B

KNEE SUPPORT DEVICE

BACKGROUND

1. Field of Invention

This invention relates to a knee support device for providing focused and conformable pressure to reduce knee pain.

2. Background of the Invention

The industry of pain relief has become a multi-million dollar industry. Medicines and devices of all kinds are produced and marketed to relieve pain and to prevent further injury. As individual's get older, their bodies begin to break down and certain parts of their bodies tend to become prone to pain. Additionally, those individuals that are active may have injuries from over strenuous use of their bodies.

In particular, individuals such as runners, jumpers and other athletes such as skiers, cyclists and soccer players put heavy stress on their knees. The muscles that surround the knee provide mobility and strength to the legs. When athletes run or jump, the kneecap alone often endures forces of 1000 to 1500 pounds. The entire knee joint is under massive stress with these kinds of activities, especially when there are imbalances in muscle strength or flexibility. In time, overuse injuries, such as tendonitis, chondromalacia, runner's and jumper's knee, illiotibial band syndrome and Osgood Schlatter's disease, may develop.

The knee joint includes the patella or kneecap which is a thick, triangular bone which articulates with the femur and covers and protects the front of the knee joint. It is attached to the tendon of the quadriceps femoris muscle, which contracts to straighten the leg. The primary functional role of the patella is knee extension. The patella increases the leverage that the tendon can exert on the femur by increasing the angle at which it acts. Injuries to the patella can be very painful.

To alleviate some of the pain, knee braces are worn on the affected leg. Conventional knee braces are generally made of a sleeve of soft material, such as Neoprene, and have a cutout for the patella. Most include some kind of buttress, usually on the lateral side, or a raised ring ('do-nut') protecting the whole patella. Furthermore, most conventional braces are 'static' where there is no actual force applied to the patella, although some conventional braces are 'dynamic' and have elasticized straps for creating dynamic, medially displacing force to the patella.

None of the conventional braces, however, include a support or pad that is placed directly under the patella that is easily conformable and moldable to the size of the user's patella to provide focused pressure to reduce knee pain.

SUMMARY OF THE INVENTION

Broadly, the present invention is a knee support device for providing focused and comfortable pressure (i.e. conforms to the size and shape of the knee and patella) to reduce knee pain. The knee support device comprises a stretchable band for encircling a portion of the user's leg, specifically the knee joint. A moldable inner support is secured to the inner surface of the band and is filled with beads allowing the moldable inner support to conform to the specific anatomy of the user's knee for maximum support and relief. The moldable inner support is only affixed to the band at its ends so that it may move freely with respect to the band. It also provides focused pressure to reduce knee pain and helps stabilize the patella to improve alignment and tracking.

The knee support device of the present invention also includes first and second adjustable straps for providing a dual locking system that offers flexible pressure and custom fit of the knee support device for maximum performance. The user places the center of the moldable inner support under the user's patella and detachably couples the first adjustable strap to the band around the leg using a hook and loop-type fastener. Next, the user detachably couples the second adjustable strap to the band by using a hook and loop-type fastener to adjust the pressure of the knee support device.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

The foregoing features and other features of the present invention will now be described with reference to the drawings of a preferred embodiment. The illustrated embodiment is intended to illustrate, but not to limit the invention. The drawings include the following:

FIG. 1 is an anterior view of a knee support device of the present invention operatively positioned about the knee joint of a user with the knee in the extension position;

FIG. 3A is a cross sectional view of the knee support device positioned about the knee joint of a user with a relatively small knee taken along on the line 3-3 of FIG. 1, according to one aspect of the present invention;

FIG. 3B is a cross sectional view of the knee support device positioned about the knee joint of a user with a relatively large knee taken along on the line 3-3 of FIG. 1, according to a second aspect of the present invention;

DETAILED DESCRIPTION OF THE PREFERRED EMBODIMENTS

The following detailed description is of the best currently contemplated modes of carrying out the invention. The description is not to be taken in a limiting sense, but is made merely for the purpose of illustrating the general principles of the invention? since the scope of the invention is best defined by the appended claims.

FIG. 1 is an anterior view of a knee support device 2 of the present invention operatively positioned about the knee joint 4 of a user 6 with the knee in the extension position. Although the knee support device 2 is shown on the right leg of the user, those skilled in the art will appreciate that the knee support device 2 could also be worn on the left leg. Therefore, any directional terminology should not be interpreted as limiting.

Figure 2:
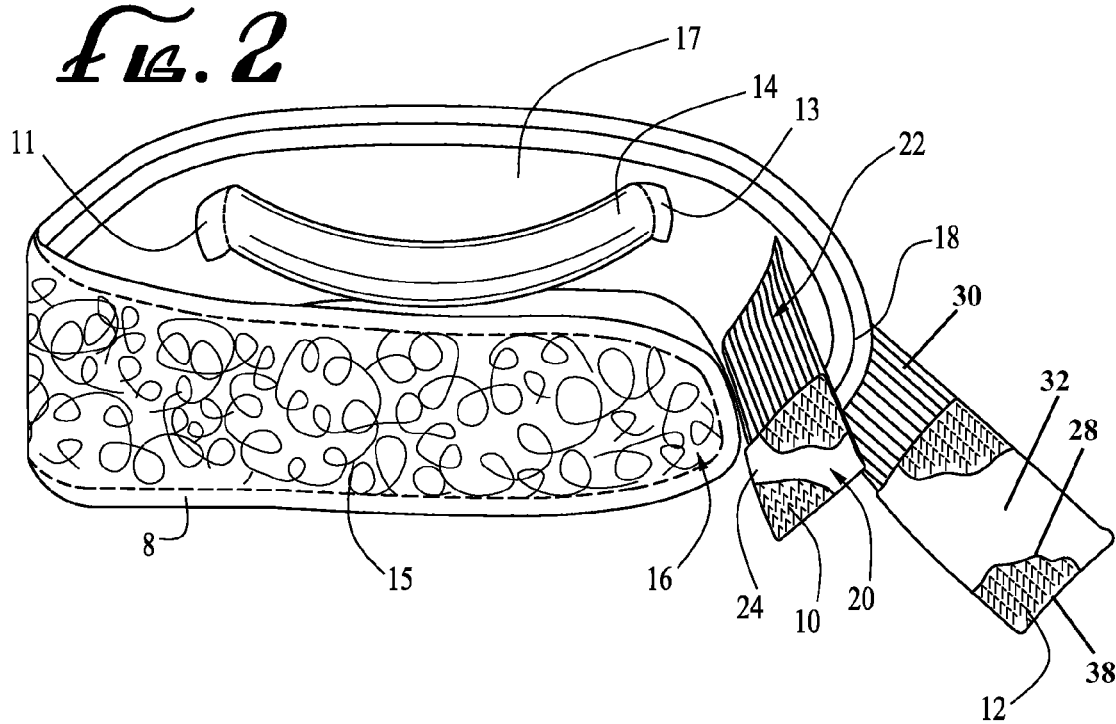
FIG. 2 is a perspective view of the knee support device alone.

FIG. 2 illustrates a perspective view of the knee support device 2 of the present invention. The knee support device 2 comprises a stretchable band 8 for encircling a portion of the user's leg, around the knee (or "knee joint"), and is made of a washable fabric, such as a mixture of cotton and stretch fiber material, for example Lycra®.

The band 8 is a generally stretchable elongate member having an outer surface 15, an inner surface 17, a first end 16 and a second end 18. The outer surface 15 is covered with loop material from a hook and loop-type fastener, such as Velcro®.

A moldable inner support 14, which includes a first end 11 and a second end 13, is affixed to the inner surface of the band 8 and is filled with beads 19 (described below) allowing the moldable inner support 14 to conform to the specific anatomy (i.e. shape and size) of the user's knee joint or patella for maximum support and relief. The moldable inner support 14 is only affixed to the band 8 at its ends 11, 13 so that it may move freely with respect to the band 8. As the moldable inner support 14 is not in a fixed position, it can mold to the shape of the user's knee joint or patella to provide individualized support to the user. The moldable inner support 14 also provides focused pressure to reduce knee pain and helps stabilize the patella to improve alignment and tracking.

A first adjustable strap 10 is attached to the inner surface 17 of the second end 18 of the band 8. The first adjustable strap 10 is made of a stretchable material, such as elastic, and comprises a first end 20, a second end 22, a first surface 24, a second surface (not shown) opposite to the first surface 24, and a first hook portion 36. The first hook portion 36, made of a hook and loop-type fastener, is attached to the first end 20 of the first surface 24 of the first adjustable strap 10 for detachably coupling the first adjustable strap 10 to the outer surface 15 of the first end 16 of the band 8 and permits adjustment of the overall size (i.e., diameter) of the knee support device 2, including the radius of curvature of the moldable inner support 14, to conform to the size of the user's leg or knee joint. The radius of curvature of the moldable inner support 14 is directly proportional to the size of the user's knee joint.

A second adjustable strap 12 is attached to the outer surface 15 of the second end 18 of the band 8. The second adjustable strap 12 is made of a stretchable material, such as elastic, and comprises a first end 28, a second end 30, a first surface 32, a second surface (not shown) opposite to the first surface 32, and a second hook portion 38. The second hook portion 38, made of a hook and loop-type fastener, is attached to the first end 28 of the first surface 32 of the second adjustable strap 12 for detachably coupling the second adjustable strap 12 to the outer surface 15 of the band 8 to permit the pressure of the moldable inner support 14 to be adjusted based upon the needs of the user. The pressure applied to the patella of the user is increased or decreased by tightening or loosening the second adjustable strap 12, respectively.

As described above, the first and second adjustable straps 10, 12 provide a dual locking system that offers flexible pressure and custom fit of the knee support device 2 for maximum performance. A user places the center of the moldable inner support 14 under his patella and removably attaches the first adjustable strap 10 to the band 8 around the leg by engaging the fibers in the hook and loop-type fastener of the first hook portion 36 with the fibers in the hook and loop-type fastener on the outer surface of the band 8. Next, the user removably attaches the second adjustable strap 12 to the band 8 by engaging the fibers in the hook and loop-type fastener of the second hook portion 36 with the fibers in the hook and loop-type fastener on the outer surface of the band 8 to adjust the pressure of the knee support device 2.

The beads 19 filling the moldable inner support 14 in the exemplary embodiment of the invention may be formed of plastic material such as low density polyethylene (LDPE) and may be injection molded or extrusion type LDPE particles or pellets. The beads 19 are rounded and free of sharp edges, with a smooth surface which enables the beads 19 to slide smoothly against one another. The beads' surface may be polished to enhance smoothness, and may be coated with a lubricating material and/or a mold suppressant such as an amide. The beads 19 provide a pad which is easily deformable and moldable to the desired position forming to the size of the user's patella providing maximum support and relief.

By only affixing the ends 11, 13 of the moldable inner support 14 to the band 8, the moldable inner support 14 can move independently of the band 8, when the knee support device 2 is placed around the user's knee joint and the radius of curvature of the moldable inner support 14 adjusts to conform to shape and size of the user's knee joint. If the user's knee joint has a relatively small diameter, the radius of curvature of the moldable inner support 14 is small resulting in a more curved moldable inner support 12. Conversely, if the user's knee joint has a relatively larger diameter, the radius of curvature of the moldable inner support 14 is large resulting in a more straight moldable inner support 14. The variable radius of curvature of the moldable inner support 12 is shown with respect to FIGS. 3A-3B and FIG. 5A-5B (discussed below).

FIG. 3A is a cross sectional view taken along on the line 3-3 of FIG. 1, illustrating the adjustability of the knee support device 2 to the size of a user's leg (specifically the knee joint), according to one aspect of the present invention. In FIG. 3A, the moldable inner support 14, filled with beads 19, conforms to the shape and size of the knee joint 21. As the leg shown in FIG. 3A is of a relatively small diameter, the moldable inner support 14 curves to fit the knee joint 21 resulting in the moldable inner support 14 having a distinct curved configuration, shown by the beads 19 conforming to the curve of the knee joint 21. To accommodate the smaller size, the second end of the band 8 overlaps the first end of the band 8.

FIG. 3B is a cross sectional view taken along on the line 3-3 of FIG. 1, illustrating the adjustability of the knee support device 2 to the size of a user's leg (specifically the knee joint), according to a second aspect of the present invention. In FIG. 3B, the moldable inner support 14, filled with beads 19, conforms to the size and shape of a knee joint 23 that is larger than the knee joint 21 shown in FIG. 3A. As the knee joint 23 shown in FIG. 3B is larger the knee joint 21 of FIG. 3A, the moldable inner support 14 is less curved (almost straight) to accommodate the larger size, shown by the alignment of the beads 19 in an almost straight line.

Figure 4:
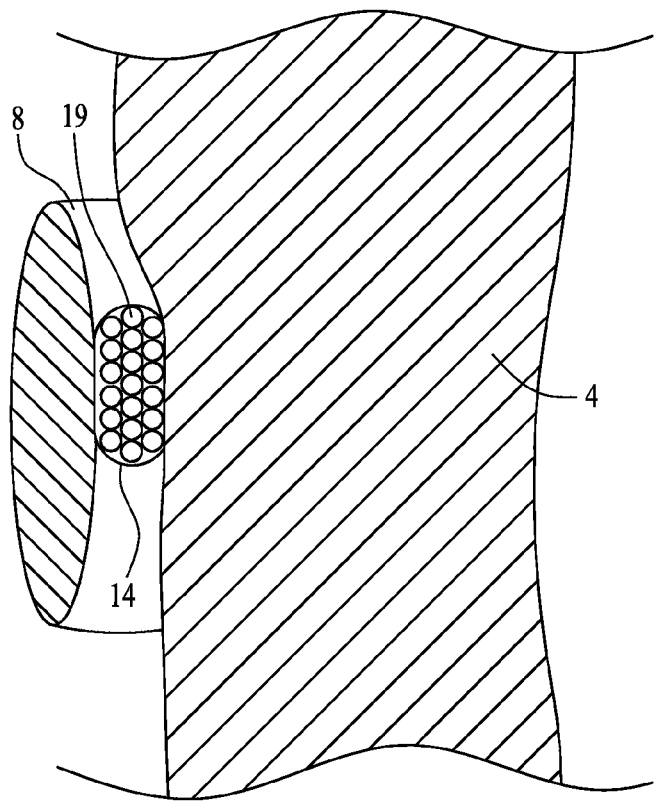
FIG. 4 is a cross sectional view of the knee support device positioned about the knee joint of a user taken along the line 4-4 of FIG. 3B.

FIG. 4 is a cross sectional view of the knee support device 2 positioned about the knee joint of a user taken along the line 4-4 of FIG. 3B. As can be seen in FIG. 4, the moldable inner support 14, filled with beads 19, is centered under the patella of the user and the band 8 encircles the knee joint 4.

Figure 5A:
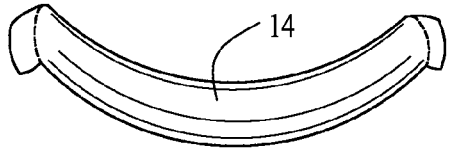
FIGS. 5A-5C show the size and shape of a moldable inner support of the knee support device positioned about a large, medium and small diameter knee joint, respectively.
Figure 5B:
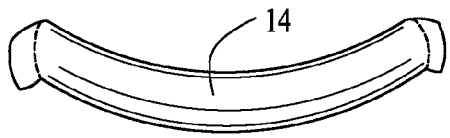
Figure 5C:
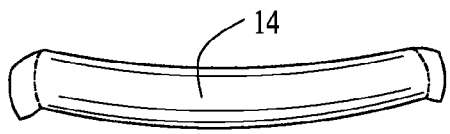

As discussed above, the moldable inner support 14 conforms to the size and shape of the user's knee joint as only its ends 11, 13 are affixed to the band 8. Placing the knee support device 2 on a knee joint having a relatively larger diameter will result in the moldable inner support 14 having a relatively large radius of curvature (i.e. the moldable inner support 14 is almost straight). (FIG. 5A) Placing the knee support device 2 on a knee joint having relatively medium diameter will result in the moldable inner support 14 having a relatively medium radius of curvature. (FIG. 5B) Placing the knee support device 2 on a knee joint having a relatively small diameter will result in the moldable inner support 14 having a relatively small radius of curvature. (FIG. 5C)

The knee support device 2 of the present invention is advantageous over conventional knee braces in that it provides focused pressure on the patella of the user. Furthermore, the device 2 has a dual locking system and is designed for more universal use by anybody as it is adjustable and provides support to the patella to alleviate symptoms of tendonitis, chondromalacia, runner's and jumper's knee, illiotibial band syndrome, Osgood Schlatter's disease and other knee conditions.

While the present invention is described above with respect to what is currently considered its preferred embodiments, it is to be understood that the invention is not limited to that described above. To the contrary, the invention is intended to cover various modifications and equivalent arrangements within the spirit and scope of the appended claims.

What is claimed is:

1. A knee support device, comprising:
    an elongate band, having an inner surface and an outer surface, for encircling a leg of a user, the band having a top edge, a bottom edge, and two side edges wherein the top edge and the bottom edge are parallel to one another and the two side edges are parallel to one another;
    a moldable inner support, having a first end and a second end, wherein the first and second ends are attached to the inner surface of the band to conform to the shape and size of the user's knee and patella and allowing the moldable inner support to move independently of the band;
    a first adjustable strap, having a first end and a second end, wherein the second end of the first adjustable strap is affixed to the inner surface of the band and wherein the first end of the first adjustable strap is removably coupled to the band; and
    a second adjustable strap, having a first end and a second end, wherein the second end of the second adjustable strap is affixed to the outer surface of the band and wherein the first end of the second adjustable strap is removably coupled to the band, wherein the band is positionable below a kneecap of the user.

2. The device of claim 1, wherein the outer surface of the band is covered with a hook and loop-type fastener.

3. The device of claim 2, wherein the first adjustable strap permits adjustment of the overall diameter of the knee support device.

4. The device of claim 3, further comprising a first hook portion attached to the first end of the first surface of the first adjustable strap for detachably coupling the first adjustable strap to the outer surface of the first end of the band; and wherein the first hook portion is a hook and loop-type fastener.

5. The device of claim 4, further comprising a second hook portion attached to the first end of the first surface of the second adjustable strap for detachably coupling the second adjustable strap to the outer surface of the band to permit the pressure of the knee support device to be adjusted based upon the needs of the user; and wherein the first hook portion is a hook and loop-type fastener.

6. The device of claim 5, wherein the first and second adjustment straps are made from elastic.

7. The device of claim 1, wherein the moldable inner support is filled with beads.

8. The device of claim 1, wherein the band is made of a mixture of cotton and stretch fiber material.

9. The device of claim 1, wherein the band can be placed on either the user's left leg or right leg.

10. The device of claim 1, wherein the moldable inner support provides focused pressure to the patella to reduce knee pain and stabilize the patella to improve alignment and tracking.

11. The device of claim 1, wherein the radius of curvature of the moldable inner support is directly proportional to the size of the knee.

12. A method for providing focused pressure to a patella of a user, comprising:
    positioning a knee support device below the knee of a user; wherein the knee support device comprises an elongate band having an inner surface and an outer surface, a moldable inner support having a first end and a second end attached the inner surface of the band allowing the moldable inner support to move independently of the band; a first adjustable strap affixed to the inner surface of the band; and a second adjustable strap affixed to the outer surface of the band;
    positioning the center of the moldable inner support under the patella to conform to the shape of the user's knee to provide focused pressure on the patella;
    removably attaching the first adjustable strap to the band for adjusting the overall diameter of the knee support device; and
    movably attaching the second adjustable strap to the band for adjusting the pressure applied to the patch by the knee support device.

* * * * *